(12) United States Patent
Jones et al.

(10) Patent No.: US 7,732,647 B2
(45) Date of Patent: Jun. 8, 2010

(54) PROCESS FOR THE PURIFICATION OF FLUOROMETHYL 1,1,1,3,3,3-HEXAFLUOROISOPROPYL ETHER (SEVOFLURANE)

(75) Inventors: Barry Jones, Martinez, GA (US); Joel Swinson, Evans, GA (US); Paul Mazzell, Aiken, SC (US)

(73) Assignee: Halocarbon Products Corporation, North Augusta, SC (US)

( * ) Notice: Subject to any disclaimer, the term of this patent is extended or adjusted under 35 U.S.C. 154(b) by 311 days.

(21) Appl. No.: 11/965,137

(22) Filed: Dec. 27, 2007

(65) Prior Publication Data

US 2009/0171128 A1    Jul. 2, 2009

(51) Int. Cl.
C07C 41/38    (2006.01)

(52) U.S. Cl. ..................... 568/682; 568/683

(58) Field of Classification Search ............ None
See application file for complete search history.

(56) References Cited

U.S. PATENT DOCUMENTS

| | | |
|---|---|---|
| 4,250,334 A | 2/1981 | Coon et al. |
| 6,100,434 A | 8/2000 | Bieniarz et al. |
| 6,469,219 B1 | 10/2002 | Khrimian et al. |
| 7,230,142 B1 | 6/2007 | Kawai et al. |
| 2004/0124076 A1 | 7/2004 | Sharratt et al. |

FOREIGN PATENT DOCUMENTS

| | | |
|---|---|---|
| WO | WO97/25303 | 7/1997 |
| WO | WO99/44978 | 9/1999 |
| WO | WO02/50005 | 6/2002 |
| WO | WO2007/019161 | 2/2007 |

*Primary Examiner*—Rosalynd Keys
(74) *Attorney, Agent, or Firm*—Hoffman & Baron, LLP

(57) ABSTRACT

A process for purifying crude fluoromethyl 1,1,1,3,3,3-hexafluoroisopropyl ether (sevoflurane). The crude sevoflurane is repeatedly washed with water under conditions and for a time sufficient to reduce the level of 1,1,1,3,3,3-hexafluoroisopropanol (HFIP) to no more than 200 ppm or no more than 100 ppm.

23 Claims, No Drawings

PROCESS FOR THE PURIFICATION OF FLUOROMETHYL 1,1,1,3,3,3-HEXAFLUOROISOPROPYL ETHER (SEVOFLURANE)

BACKGROUND OF THE INVENTION

1. Field of the Invention

The present invention relates generally to the production and purification of fluoromethyl 1,1,1,3,3,3-hexafluoroisopropyl ether (sevoflurane), which is used as an inhalation anesthetic.

2. Description of Related Art

There are several known methods for the production of sevoflurane, particularly by the reaction of formaldehyde (or a formaldehyde equivalent such as paraformaldehyde or trioxane), hydrogen fluoride (HF), and 1,1,1,3,3,3-hexafluoroisopropanol (HFIP). U.S. Pat. No. 4,250,334 describes a process in which HFIP is added to a mixture of a stoichiometric excess of paraformaldehyde and HF plus sufficient sulfuric acid to sequester most of the water formed in the reaction. WO 97/25303 describes a process for the production of sevoflurane in which essentially pure bis(fluoromethyl) ether (BFME) is allowed to react with HFIP and sulfuric acid. U.S. Pat. No. 6,469,219 ('219) describes a process in which HFIP and a formaldehyde equivalent are allowed to react with excess HF under distillative or extractive conditions in order to produce sevoflurane.

In all of these processes, unreacted HFIP may remain in the product mixture, as well as BFME, methyl hexafluoroisopropyl ether (MHFIP), polyethers containing the HFIP and formaldehyde moieties, and various other undesired species. These impurities must be removed from the crude sevoflurane product in order to obtain a pharmaceutically acceptable form of the material. For example, a pharmaceutically acceptable form of sevoflurane should contain less than about 20 ppm of HFIP.

Many impurities in crude sevoflurane product can be removed by distillation. HFIP, however, is difficult to distil from sevoflurane since the two molecules have similar boiling points and may form an azeotropic mixture. Simple washing of the crude sevoflurane product with water to remove HFIP has been reported, in US 2004/0124076 for example, to be inefficient, time consuming, and costly.

Thus, Example 1 of European Patent Application EP 703 450 describes a process for producing sevoflurane by heating a reaction mixture of sulfuric acid, hydrogen fluoride, and paraformaldehyde. The resulting crude product was extracted three times with water. As a result of prosecution of the corresponding U.S. application (resulting in issuance of U.S. Pat. No. 7,230,142), the mixture was later shown to contain about 4.7% HFIP. Such an amount is unacceptable for clinical grade sevoflurane.

WO 99/44978 and related U.S. Pat. No. 7,230,142 describe a process for the removal of HFIP from sevoflurane by performing aqueous base washes of crude sevoflurane. This process requires careful control of the amount of base used in proportion to the amount of HFIP present, as well as careful temperature control in order to avoid the conversion of some of the sevoflurane to sevoflurane compound A (1,1,1,3,3-pentafluoroisopropenyl fluoromethyl ether), a highly toxic and undesired side product. Prolonged processing with repeated sampling and analysis is required in order to ensure adequate removal of HFIP without formation of excess sevoflurane compound A. Thus, this approach has the disadvantages of complexity and added cost in the production process.

U.S. Pat. No. 7,230,142 also describes two comparative examples wherein a mixture of HFIP and sevoflurane is washed with pure water in an attempt to remove HFIP. In one comparative example, an initial amount of 10% HFIP in a mixture with sevoflurane was reduced to 3.4% HFIP by washing with water. In another comparative example, an initial amount of 0.25% HFIP in a mixture with sevoflurane was not reduced at all by washing with water.

WO 02/50005 and related US 2004/0124076 describe a process for purifying a crude sevoflurane product mixture by contacting a crude composition of sevoflurane and HFIP with a modifier to alter the vapor pressure of the ether and/or alcohol. The ether and alcohol then may be separated by distillation. The modifier is typically a compound which contains a group capable of bonding with or at least of donating electrons to HFIP, such as an amino group. The use of such a modifier adds cost and complexity to the production process since the modifier must be completely removed from both (i) the sevoflurane and (ii) the unreacted HFIP that is recycled back into the reaction phase. The modifier then must either be recycled or isolated for disposal. Odor issues are also of concern when amines or thiols are used as the modifier.

Middleton and Lindsey in the Journal of the American Chemical Society, 1964, 86: 4948-4952 have described azeotropes of fluorinated secondary alcohols, such as hexafluoroisopropanol, in which the normal boiling point is higher than the boiling point of the alcohol. Methods of breaking these azeotropes were also described, but applications of these azeotropes were not described.

International PCT application US2006/030046 of Halocarbon Products Corporation describes a process of purifying a crude sevoflurane product containing unacceptably high levels of HFIP. In this process, the crude sevoflurane product is combined with sufficient water to produce a multiphase mixture, the multiphase mixture is fractionally distilled, and substantially pure sevoflurane is removed from the fractionally distilling multiphase mixture. A disadvantage of this process is that the distillation may add to the cost and complexity of the process.

Other proposed methods of sevoflurane synthesis, such as that described in U.S. Pat. No. 6,100,434, avoid this difficult sevoflurane/hexafluoroisopropanol separation by using more complicated methods of synthesis.

What is still needed is a simple method for the efficient separation of sevoflurane and HFIP. Surprisingly, the inventors have discovered a simple, inexpensive, and convenient process for the purification of crude sevoflurane that results in purified sevoflurane.

SUMMARY OF THE INVENTION

The present invention is a process for obtaining purified fluoromethyl 1,1,1,3,3,3-hexafluoroisopropyl ether (sevoflurane) from crude sevoflurane. In the process, the crude sevoflurane is combined with water in an amount sufficient to produce a multiphase mixture. The multiphase mixture has both an aqueous phase and a sevoflurane phase. The aqueous phase and the sevoflurane phase are contacted with each other under conditions and for a period of time sufficient to extract at least a portion of the HFIP from the sevoflurane phase into the aqueous phase. The phases of the multiphase mixture are then separated without fractional distillation. These steps may be repeated, if necessary, until purified sevoflurane comprising no more than an acceptable amount of HFIP is isolated. The HFIP is removed from the crude sevoflurane without contacting the crude sevoflurane with an aqueous basic solution.

In one embodiment, crude sevoflurane comprises sevoflurane, more than 200 ppm 1,1,1,3,3,3-hexafluoroisopropanol (HFIP) and, optionally, hydrogen fluoride (HF). The purified sevoflurane isolated in this embodiment comprises no more than 200 ppm, preferably no more than about 150 ppm HFIP, more preferably no more than about 100 ppm, even more preferably no more than about 20 ppm, and most preferably no more than about 10 ppm HFIP.

In another embodiment, crude sevoflurane comprises sevoflurane, more than 100 ppm 1,1,1,3,3,3-hexafluoroisopropanol (HFIP) and, optionally, hydrogen fluoride (HF). The purified sevoflurane isolated in this embodiment comprises no more than 100 ppm HFIP, preferably no more than about 20 ppm, and more preferably no more than about 10 ppm HFIP.

The crude sevoflurane of the invention may be part of a crude sevoflurane product. The crude sevoflurane product may be produced by reacting HFIP, formaldehyde and hydrogen fluoride (HF). Preferably, the crude sevoflurane product is produced by reacting HFIP, formaldehyde and a stoichiometric excess of HF.

The process of the invention may further comprise reducing the amount of HF in the crude sevoflurane prior to combining the crude sevoflurane with water.

The process of the invention may be conducted in a continuous manner.

In yet another embodiment of the invention, purified fluoromethyl 1,1,1,3,3,3-hexafluoroisopropyl ether (sevoflurane) may be obtained by producing crude sevoflurane by reacting HFIP, formaldehyde and HF and then reducing the amount of HF in the crude sevoflurane. Next, the crude sevoflurane is combined with water in an amount sufficient to produce a multiphase mixture comprising an aqueous phase and a sevoflurane phase. The aqueous phase and the sevoflurane phase are contacted with each other under conditions and for a time sufficient to extract at least a portion of the HFIP from the sevoflurane phase into the aqueous phase. The phases of the multiphase mixture are separated without fractional distillation.

The steps of combining the crude sevoflurane with water in an amount sufficient to produce a multiphase mixture comprising an aqueous phase and a sevoflurane phase, contacting the aqueous phase and the sevoflurane phase with each other under conditions and for a time sufficient to extract at least a portion of the HFIP from the sevoflurane phase into the aqueous phase, and separating the phases of the multiphase mixture without fractional distillation, may, if necessary, be repeated. Purified sevoflurane comprising an acceptable amount of HFIP is then isolated. The removal of HFIP from the crude sevoflurane occurs without contacting the crude sevoflurane with an aqueous basic solution.

In this embodiment of the invention, an acceptable amount of HFIP in the purified sevoflurane is no more than 200 ppm, preferably no more than about 150 ppm HFIP, more preferably no more than about 100 ppm, even more preferably no more than about 20 ppm, and most preferably no more than about 10 ppm HFIP.

Preferably, the process of the reaction occurs wherein the crude sevoflurane is produced by reacting HFIP, formaldehyde, and a stoichiometric excess of HF.

This embodiment of the invention may be conducted in a continuous manner.

DETAILED DESCRIPTION OF THE INVENTION

The invention relates to the purification of crude sevoflurane. In one embodiment, crude sevoflurane refers to fluoromethyl 1,1,1,3,3,3-hexafluoroisopropyl ether that contains more than 200 ppm 1,1,1,3,3,3-hexafluoroisopropanol (HFIP). A crude sevoflurane product refers to the product of a reaction used to prepare crude sevoflurane. For example, a crude sevoflurane product refers to a product mixture comprising crude sevoflurane, any by-products of the reaction, and unreacted starting materials.

The crude sevoflurane contains HFIP from any source. For example, unreacted HFIP is typically present in a crude sevoflurane product. The amount of unreacted HFIP in the crude sevoflurane product depends on the particular reaction used to produce the sevoflurane, and the conditions under which the reaction is carried out. There may, for example, be more than 100 ppm, more than 200 ppm more than 1,000 ppm, more than 1%, or more than 5% HFIP in crude sevoflurane or crude sevoflurane product.

The reaction that produces a crude sevoflurane product may be any reaction that results in sevoflurane. In one embodiment, crude sevoflurane product is produced by reacting HFIP, formaldehyde and hydrogen fluoride (HF). Preferably, the sevoflurane is produced by reacting HFIP, formaldehyde, and a stoichiometric excess of HF. Such a process is described in U.S. Pat. No. 6,469,219 ('219). The term "formaldehyde," as used herein, means not only formaldehyde per se, but also any equivalent of formaldehyde, for example, formaldehyde polymers such as trioxane and paraformaldehyde. The crude sevoflurane product may include HF, for example, from unreacted reagent, byproduct, or azeotropes from distilling a crude sevoflurane product.

In a preferred process, the amount of HF in the crude sevoflurane product is reduced before the first combining of crude sevoflurane with water. The amount of HF may be reduced in accordance with known procedures such as those described in the '219 patent, at, for example, Examples 4 through 6, to obtain a second crude sevoflurane product. Examples 4, 5, and 6 of the '219 patent are incorporated herein by reference.

The crude sevoflurane and the crude sevoflurane product may or may not contain a solvent. Some suitable solvents include the solvents disclosed in U.S. Pat. No. 6,469,219, e.g., chlorofluorocarbons, chlorohydrocarbons, perfluorohydrocarbons, perfluoroethers, and hydrocarbons. Some examples of specific solvents include 1,2,3-trichloropropane, isooctane and perfluoromethyldecalin. The solvent may also be a mixture, such as a mixture of more than one solvent mentioned above, and Krytox (DuPont). The preferred solvent is HC-0.8 oil, which is a mixture of tetrachlorohexafluorobutanes commercially available from Halocarbon Products Corporation. The disclosure of these and other solvents in U.S. Pat. No. 6,469,219 is incorporated herein by reference. Crude sevoflurane typically contains mostly sevoflurane, and no additional solvent.

Purified sevoflurane refers to crude sevoflurane that has been subjected to the process of the invention. The amount of HFIP in the purified sevoflurane has been reduced to an acceptable level. Products in the intermediate stages of the purification process leading to purified sevoflurane are referred to as crude sevoflurane if they contain more than an acceptable amount of HFIP.

In one embodiment, crude sevoflurane contains more than 200 ppm HFIP, and the acceptable amount of HFIP in the purified sevoflurane isolated as a result of the invention is no more than 200 ppm, preferably no more than about 150 ppm, more preferably no more than about 100 ppm, even more preferably no more than about 20 ppm and most preferably no more than about 10 ppm. In another embodiment, crude sevoflurane contains more than 100 ppm HFIP, and the acceptable amount of HFIP in the purified sevoflurane isolated as a result of the invention is no more than 100 ppm, preferably no more than about 20 ppm and more preferably no more than about 10 ppm. In yet another embodiment, crude sevoflurane contains more than 20 ppm HFIP, and the acceptable amount of HFIP in the purified sevoflurane isolated as a result of the invention is no more than 20 ppm, preferably no more than about 10 ppm. In another embodiment, crude sevoflurane contains more than 10 ppm HFIP, and the acceptable amount of HFIP in the purified sevoflurane isolated as a result of the invention is no more than 10 ppm.

The process of the invention provides for the crude sevoflurane to be contacted with water. The water with which the crude sevoflurane is combined is water from any source, and is non-basic. Preferably, the water has a pH of about 7 or less. Suitable sources of water include most industrial and domestic supplies of water. Such water may be used directly from a tap. The tap water may optionally be further purified, such as by distillation, reverse osmosis, or passage through an ion exchange column, although it is usually not necessary to do so.

Sufficient water is added to the crude sevoflurane to form a multiphase mixture comprising at least a sevoflurane phase and an aqueous phase. The quantity of water added can be determined empirically, but the quantity is limited on the one hand by the necessity to remove substantially all of the HFIP from the sevoflurane, while on the other hand minimizing the amount of product lost due to its solubility in water. In a preferred embodiment of this invention, each extraction step has a wt/wt. ratio of water to crude sevoflurane as low as 1:500, preferably 1:400, and more preferably 1:300. The ratio of water to crude sevoflurane may be as high as 200:1, preferably 150:1, and more preferably 100:1. Suitable ranges of water may be obtained by combining any minimum amount with any maximum amount.

The step of contacting the aqueous phase and the sevoflurane phase with each other is carried out by methods and with equipment that are known in the art. Equipment design should be chosen so as to ensure that intimate contacting of the phases is achieved efficiently. For example, a gravity column with no agitation preferably employs "packing" or obstacles to promote turbulence to mix both phases.

In a batch process, the multiphase mixture may be shaken manually; or stirred, mixed or agitated mechanically. In a continuous process, the contacting of the sevoflurane phase and water phase may be accomplished using continuous extraction methods and equipment well known in the art. Such equipment includes, for example, mixer-settlers, gravity columns with no agitation, gravity columns with agitation and centrifugal devices. The efficiency of continuous contacting may be increased by using counter-current flows, as is also known in the art.

The phases are contacted in a suitable vessel under conditions and for a period of time suitable to extract at least a significant portion of the HFIP remaining in the sevoflurane layer into the aqueous layer. The phases may be contacted at any convenient pressure and temperature. For example, the phases may be contacted at temperatures between about 1 and about 60 degrees centigrade. Contacting the phases is most conveniently carried out at ambient temperature (e.g., about 10° C. to about 30° C., preferably about 15° C. to about 25° C.) and atmospheric pressure.

The phases of the multiphase mixture are then separated from each other by any method known in the art, except fractional distillation. The method of separation and time required to effect separation may vary depending, for example, on the method of contacting employed, the type of vessel used, the number of phases, etc. For example, in a gravity column containing packing, the type of packing may alter the time required for separation of the phases; in, a separatory funnel, however, the phase separation could be visually observed and the layers separated. In most cases, the aqueous phase is discarded following phase separation.

When the removal of the HFIP is carried out in a batch manner, the purification steps of the invention, e.g., (a) combining the crude sevoflurane with water to form a multiphase mixture, (b) contacting the aqueous phase and the sevoflurane phase with each other, and (c) separating the phases of the multiphase mixture without fractional distillation, are repeated, if necessary, until the level of HFIP in the sevoflurane phase is reduced to no more than an acceptable amount, e.g., 200 ppm, preferably to no more than about 150 ppm, more preferably to no more than about 100 ppm, even more preferably to no more than about 20 ppm and most preferably to no more than about 10 ppm, as the case may be. If purification is not complete after the first washing, the purification steps are repeated a sufficient number of times to obtain the desired reduction of HFIP. The number of repetitions may, for example, be a minimum of 2, typically about 4, and more typically about 6. The maximum number of repetitions is about 30, typically about 25, and more typically about 20. In one embodiment, the number of repetitions is about 10 to about 15.

The contact time is determined primarily by the efficiency of removal of HFIP and convenience. Any contact time that results in removal of a significant amount of HFIP is suitable. In a batch process, the phases may, for example, be contacted with each other for about five minutes to about two hours, and preferably about fifteen minutes to about one hour.

When the removal of the HFIP is carried out in a continuous manner, the aqueous phase containing HFIP is continuously removed, and replaced with fresh water. Therefore, it is not necessary to repeat the steps. The contact time in a continuous process may be as short, for example, as about two seconds, about ten seconds, about thirty seconds, or about sixty seconds. The contact time generally will not be more than about 24 hours, and more typically not more than about ten hours or not more than about two hours.

In an additional preferred embodiment of the invention, the process for obtaining a purified sevoflurane comprises producing crude sevoflurane, and reducing the amount of HF contained in the crude sevoflurane, prior to further purification. The preferred method of producing crude sevoflurane is described above and in U.S. Pat. No. 6,469,219 ('219). The description of the synthesis of sevoflurane in the '219 patent is incorporated herein by reference.

The present invention may be better understood by reference to the following examples. The following examples illustrate the present invention and are not intended to limit the invention or its scope in any manner.

Example 1

Crude sevoflurane, previously prepared from HFIP, HF, and formaldehyde (trioxane) by the reactive distillation process described in U.S. Pat. No. 6,469,219, is cooled until two layers are formed. The organic layer containing predominantly sevoflurane is isolated. This crude sevoflurane product then is washed eight times with water at ambient temperature and atmospheric pressure. After the final wash, the sevoflurane layer contains less than 10 ppm of HFIP.

Example 2

Crude sevoflurane, previously prepared from HFIP, HF, and formaldehyde (trioxane) by the reactive distillation process described in U.S. Pat. No. 6,469,219, is cooled until two layers are formed. The organic layer containing predominantly sevoflurane is isolated. This crude sevoflurane product then is washed four times, each for about thirty minutes with 50% by weight water at ambient temperature and atmospheric pressure. After the final wash, the sevoflurane layer contains less than 10 ppm of HFIP.

Example 3

In a continuous washing process sevoflurane, previously prepared from HFIP, HF, and a formaldehyde equivalent by the reactive distillation process described in U.S. Pat. No. 6,469,219, is cooled until two layers are formed. The organic layer containing predominantly sevoflurane is isolated and passes down a 1 inch diameter by 5 feet high column under gravity conditions. The column is packed with plastic packing to promote turbulence. Simultaneously, water is passing counter-currently up the column. The flow rate of the crude sevoflurane is 0.5 kg/hr and the flow rate of water is 1.0 kg/hr. Purified sevoflurane leaving the bottom of the tube contains less than 10 ppm of HFIP.

While there have been described what are presently believed to be the preferred embodiments of the invention, those skilled in the art will realize that changes and modifications may be made thereto without departing from the spirit of the invention and it is intended to claim all such changes and modifications as fall within the true scope of the invention.

The invention claimed is:

1. A process for obtaining purified fluoromethyl 1,1,1,3,3-hexafluoroisopropyl ether (sevoflurane) from crude sevoflurane that comprises sevoflurane and more than 200 ppm 1,1,1,3,3,3-hexafluoroisopropanol (HFIP), the process comprising:
   a) combining the crude sevoflurane with water in an amount sufficient to produce a multiphase mixture comprising an aqueous phase and a sevoflurane phase;
   b) contacting the aqueous phase and the sevoflurane phase with each other under conditions and for a period of time sufficient to extract at least a portion of the HFIP from the sevoflurane phase into the aqueous phase;
   c) separating the phases of the multiphase mixture without fractional distillation;
   d) if necessary, repeating steps a) through c) until the level of HFIP in the sevoflurane phase is reduced to no more than 200 ppm; and
   e) isolating purified sevoflurane comprising no more than 200 ppm of HFIP;
   wherein the HFIP is removed from the crude sevoflurane without contacting the crude sevoflurane with an aqueous basic solution.

2. The process according to claim 1, wherein the purified sevoflurane comprises no more than about 100 ppm HFIP.

3. The process according to claim 1, wherein the purified sevoflurane comprises no more than about 20 ppm HFIP.

4. The process according to claim 1, wherein the purified sevoflurane comprises no more than about 10 ppm HFIP.

5. The process according to claim 1, wherein the crude sevoflurane is part of a crude sevoflurane product.

6. The process according to claim 5, wherein the crude sevoflurane product is produced by reacting HFIP, formaldehyde and hydrogen fluoride (HF).

7. The process according to claim 6, wherein the crude sevoflurane product is produced by reacting HFIP, formaldehyde and a stoichiometric excess of HF.

8. The process according to claim 1, wherein the crude sevoflurane further comprises hydrogen fluoride (HF), and the process further comprises reducing the amount of HF in the crude sevoflurane before step a).

9. The process according to claim 1, which is conducted in a continuous manner.

10. A process for obtaining purified fluoromethyl 1,1,1,3,3-hexafluoroisopropyl ether (sevoflurane), the process comprising:
   i) producing crude sevoflurane by reacting 1,1,1,3,3,3-hexafluoroisopropanol (HFIP), formaldehyde and hydrogen fluoride (HF);
   ii) reducing the amount of HF in the crude sevoflurane;
   iii) combining the crude sevoflurane with water in an amount sufficient to produce a multiphase mixture comprising an aqueous phase and a sevoflurane phase;
   iv) contacting the aqueous phase and the sevoflurane phase with each other under conditions and for a time sufficient to extract at least a portion of the HFIP from the sevoflurane phase into the aqueous phase;
   v) separating the phases of the multiphase mixture without fractional distillation;
   vi) if necessary, repeating steps iii) through v) until the level of HFIP in the sevoflurane phase is reduced to no more than 200 ppm; and
   vii) isolating purified sevoflurane comprising no more than 200 ppm HFIP;
wherein the HFIP is removed from the crude sevoflurane without contacting the crude sevoflurane with an aqueous basic solution.

11. The process according to claim 10, wherein the purified sevoflurane comprises no more than about 100 ppm HFIP.

12. The process according to claim 10, wherein the purified sevoflurane comprises no more than about 20 ppm HFIP.

13. The process according to claim 10, wherein the purified sevoflurane comprises no more than about 10 ppm HFIP.

14. The process according to claim 10, wherein the crude sevoflurane is produced by reacting HFIP, formaldehyde, and a stoichiometric excess of HF.

15. The process according to claim 10, which is conducted in a continuous manner.

16. A process for obtaining purified fluoromethyl 1,1,1,3,3-hexafluoroisopropyl ether (sevoflurane) from crude sevoflurane that comprises sevoflurane and more than 100 ppm 1,1,1,3,3,3-hexafluoroisopropanol (HFIP), the process comprising:
   a) combining the crude sevoflurane with water in an amount sufficient to produce a multiphase mixture comprising an aqueous phase and a sevoflurane phase;
   b) contacting the aqueous phase and the sevoflurane phase with each other under conditions and for a period of time sufficient to extract at least a portion of the HFIP from the sevoflurane phase into the aqueous phase;
   c) separating the phases of the multiphase mixture without fractional distillation;
   d) if necessary, repeating steps a) through c) until the level of HFIP in the sevoflurane phase is reduced to no more than 100 ppm; and
   e) isolating purified sevoflurane comprising no more than 100 ppm of HFIP;

wherein the HFIP is removed from the crude sevoflurane without contacting the crude sevoflurane with an aqueous basic solution.

17. The process according to claim 16, wherein the purified sevoflurane comprises no more than about 20 ppm HFIP.

18. The process according to claim 16, wherein the purified sevoflurane comprises no more than about 10 ppm HFIP.

19. The process according to claim 16, wherein the crude sevoflurane is part of a crude sevoflurane product.

20. The process according to claim 19, wherein the crude sevoflurane product is produced by reacting HFIP, formaldehyde and hydrogen fluoride (HF).

21. The process according to claim 20, wherein the crude sevoflurane product is produced by reacting HFIP, formaldehyde and a stoichiometric excess of HF.

22. The process according to claim 16, wherein the crude sevoflurane further comprises hydrogen fluoride (HF), and the process further comprises reducing the amount of HF in the crude sevoflurane before step a).

23. The process according to claim 16, which is conducted in a continuous manner.

* * * * *